| United States Patent [19] | [11] Patent Number: 4,879,114 |
|---|---|
| Catsimpoolas et al. | [45] Date of Patent: Nov. 7, 1989 |

[54] LIPIDS FROM OMENTUM AND METHODS FOR COSMETIC USE

[75] Inventors: Nicholas Catsimpoolas, Newton Centre; Ahmad R. Kamarei, Arlington; Ann L. Griffith, Newton Centre, all of Mass.; Robert S. Sinn, New York, N.Y.

[73] Assignee: Angio-Medical Corporation, Avenue of the Americas, N.Y.

[21] Appl. No.: 811,505

[22] Filed: Dec. 20, 1985

[51] Int. Cl.$^4$ .................. A61K 35/12; A61K 7/42; A61K 7/32; A61K 7/06

[52] U.S. Cl. .................. 424/95; 514/557; 514/844; 514/845; 514/846; 514/847; 424/59; 424/65; 424/70

[58] Field of Search ............ 514/557, 25, 21, 770, 514/844, 845, 846, 847, 848, 880, 881, 886, 887; 424/95, 104, 65, 70, 59

[56] References Cited

U.S. PATENT DOCUMENTS

| 3,185,627 | 5/1965 | Kass | 424/59 X |
|---|---|---|---|
| 4,421,769 | 12/1983 | Dixon et al. | 514/844 |
| 4,474,763 | 10/1984 | Lubowe | 514/21 |
| 4,563,346 | 1/1986 | Deckner | 514/847 |
| 4,673,667 | 6/1987 | Catsimpoolas | 514/54 X |
| 4,710,490 | 12/1987 | Catsimpoolas et al. | 514/25 |
| 4,716,224 | 12/1987 | Sakurai et al. | 514/844 X |

FOREIGN PATENT DOCUMENTS

| 170707 | 10/1983 | Japan | 514/846 |
|---|---|---|---|
| 8101514 | 6/1981 | PCT Int'l Appl. | 424/95 |
| 825075 | 5/1981 | United Kingdom | 514/846 |

OTHER PUBLICATIONS

Goldsmith et al., "Lipid Angiogenic Factor From Omentum", JAMA., Oct. 19, 1984, vol. 252 No. 15, pp. 2034–2036.

Primary Examiner—John S. Maples
Attorney, Agent, or Firm—Felfe & Lynch

[57] ABSTRACT

36 Lipid extracts and lipid fractions from mammalian omenta containing mostly lipids are used cosmetically for skin conditions, skin care and cosmetic products which products have skin softening applications without skin irritation, greasiness or mutagenic effect. These materials with and without ganglioside are used for skin conditions such as keratosis, white spots and the like.

24 Claims, No Drawings

LIPIDS FROM OMENTUM AND METHODS FOR COSMETIC USE

This application concerns cosmetic use of isolated and purified lipids from mammalian omenta.

BACKGROUND

This invention relates to cosmetic applications as in creams and lotions for skin care.

The patent literature shows various cosmetic claims containing various waxes, oils, alcohols and fats. Some of these compositions are used as cosmetic bases see U.S. Pat. No. 2,532,206 issued Nov. 28, 1950 to Taub et al. U.S. Pat. No. 2,988,484 issued to Barsky et al. June 13, 1961 and U.S. Pat. No. 3,826,845 issued July 30, 1974 to Tsunesuke Suyama et al., U.S. Pat. No. 3,846,556 issued Nov. 5, 1974 to Handjani nee Vila et al. and U.S. Pat. No. 4,401,664 issued Aug. 30, 1983 to Ingeborg Scheuffgen. Many of these cosmetics are used to increase elasticity and tightening of the skin and often may have herbal or other plant extracts included. We note U.S. Pat. No. 4,382,961 issued May 10, 1983 to Nedeczky nee Gardy et al. using sunflower extract.

Other creams are used for softening the skin and relieving chapping, soreness and dryness. Here we note U.S. Pat. No. 2,520,980 issued Sept. 5, 1980 to Maryan Terkel et al. which also contains dicholesterylether and/or cholesterol. Still other creams are used for antiperspirants as in U.S. Pat. No. 2,783,181 issued Feb. 26, 1957 to Hyman Henkin et al. using glycerine, spermaceti wax, mineral oil and also U.S. Pat. No. 2,893,918 issued July 7, 1959 to Harold A. Abramson containing alumminum chloride.

Still other creams with a lipid type base are used as skin cleansers as in U.S. Pat. No. 2,809,166 issued Oct. 8, 1957 to George E. Morris or in soaps as in U.S. Pat. No. 3,598,746 issued Aug. 10, 1971 to Thaddeus John Kaniechi et al. and U.S. Pat. No. 3,548,056 issued Dec. 15, 1970 to Edward Eigen et al. Most of the oils and fats used are from plants such as, cocoa butter, linseed oil, soybean oil, sesame oil, corn oil, and beeswax. See U.S. Pat. No. 3,222,252 issued Dec. 7, 1965 to Heinz J. Kraus and U.S. Pat. No. 4,165,385 issued Aug. 21, 1979 to Lefebre. Use of petrolatum is common but this material is not readily absorbed as noted in U.S. Pat. No. 2,954,325 issued Sept. 27, 1960 to Elizabeth von Baumann. Hydrocarbon use is also found as in U.S. Pat. No. 3,886,287 issued May 27, 1975 to Kobayashi et al.

Use of animal fats and oils are found less frequently, such as mink oil obtained under quite special costly conditions from under the hide layer. See above patent which uses a process of several weeks to obtain material. Milk is also used as in U.S. Pat. No. 3,959,491 issued May 25, 1976 to Young et al. Proteins are used as in 3,548,056 cited above in soap or in 3,904,748 issued Sept. 9, 1975 to Eckert et al. for hair and lanolin is used (U.S. Pat. No. 4,066,789 issued Jan. 3, 1978 to Mores et al but mostly in a base. Nieper et al in U.S. Pat. No. 3,274,063 issued Sept. 20, 1966 employ magnesium aspartate in cosmetic cream.

SUMMARY

Omental lipid materials are found to be useful as cosmetics for skin creams and such for topical use as skin softeners having an emollient, softening and smoothing effect and safe to use in the presence of cuts and abrasions and in skin conditions such as keratosis and irritations.

DESCRIPTION

A novel use of mammalian omental extracts has been found to be useful in the softening, moisturizing and smoothing of skin and reduction of calluses and white spots thereon. It is therefore useful as a skin cream or lotion. It is also useful in achieving accelerated tanning as well. Therefore less time need be spent in the sun to achieve the tanning effect and since such sun exposure is well known to lead to skin conditions such as melanoma or other skin cancers it can also be useful to prevent such conditions.

The omentum is extracted as below. Different mammals can be used such as feline, bovine, ovine or porcine omentum. Best results on skin are found with porcine omentum.

Omental materials are used in wound healing as described in our—copending application filed Dec. 4, 1985 S.N. 805,206 now allowed hereby incorporated by reference. These omental materials are also used in angiogenesis for myocardial conditions such as myocardial infarcts, angina, vascular or coronary inplants, angioplasty as described in our copending application filed Dec. 20, 1985 S.N. 811,375 now allowed hereby incorporated by reference. We also note the copending application S.N. 811,894 and Filed Dec. 20, 1985 showing bone healing of omental materials hereby incorporated by reference.

Preparation of Cosmetic Materials from Omentum (1a) Preparation of the Total Lipid Extract from feline Omentum The method of Goldsmith et al. J. Amer. Med. Association (1984) 252:2034–2036 was used. Also see copending U.S. application S.N. 642,624 filed Aug. 20 1984 now U.S. Pat. No. 4,699,788 issued Oct. 13, 1987 both of the above references being hereby incorporated by reference. In another co-pending application U.S. Ser. No. 782,724 now U.S. Pat. No. 4,710,490 issued Dec. 1, 1987, hereby incorporated by reference various omental extracts are analyzed and their components described. Supercritical gas extraction can also be used to extract omental lipids as in copending U.S. application Ser. No. 793,622 filed Oct. 31, 1985 by Kamarei.

The omentum was weighed, spread out on to a plastic surface and cut into approximately 4 cm pieces using surgical scissors. The omental pieces (which range in weight from 30 to 66 gm per cat) were placed in a Waring Blender containing 300 ml of phosphate buffered saline (PBS) precooled to 4° C.

Homogenization was performed for 5 minutes at 20,500 rpm. The resulting homogenate was centrifuged in 250 ml plastic bottles at 1600 g in a refrigerated centrifuge at 4° C. for 20 minutes. After centrifugation, three fractions were visible in the bottles, i.e. a pellet, a turbid homogenate and a floating cream colored cake.

For the preparation of the total lipid extract, the cake was removed after decantation of the homogenate and weighed. The blender as well as all the solutions were pre-cooled at 4° C. for one hour before use. The cake was homogenized in a Waring blender for 2 min with chloroform/methanol (2:1, v/v) solvent at room temperature at a ratio of 1 gm cake to 10 ml of solvent. The particulate matter was removed by centrifugation at 2000 g in a clinical centrifuge at room temperature for 10 minutes. The clear supernatant was then subjected to rotary evaporation at 37° C. under vacuum to remove the chloroform-methanol mixture. The fatty material was weighed and is referred to as the "total lipid extract", also known as the lipid extract and/or the chloroform-methanol extract or CME, and the CMFr or chloroform-methanol extracted fraction of the omentum.

(1b) Preparation of Feline Omentum Neutral Lipids

Twenty-three grams of total lipid extract, CMFr, were dissolved in 120 ml hexane. Eighty ml of 95% ethanol was added and mixed thoroughly. The phases were allowed to separate, then the lower phase was removed and the upper phase (hexane layer) was reextracted with another 80 ml of 95% ethanol. The lower phases were combined and backwashed with 80 ml hexane. The hexane phases were combined and dried by rotary evaporation. The weight of the neutral lipids (mostly triglycerides) was 22.8 gm, or 98.2% yield. This hexane fraction is also known as the neutral lipid fraction from omentum or the HxCMFr (hexane phase material from the 95% Ethanol Hexane partition of the CMFr).

Other hydrocarbons (e.g., pentane, cyclohexane, cyclopentane, benzene, etc.) can be used instead of hexane for the above separation. Methanol, n-propanol, and acetonitrile can be used instead of ethanol for the above separation. Other methods can also be used as seen and obvious to those skilled in the art in Kates, M. (1972) "Techniques of Lipidology: Isolation, Analysis, and Identification of Lipids", (North-Holland Elsevier P.269–610) hereby incorporated by reference. These methods among others may include acetone precipitation, solvent partition using countercurrent distribution, column chromatography, and/or high pressure liquid chromatography. A $N_2$ atmosphere for example can be used to prevent oxidation during extraction.

(1c) Analysis of Fatty Acids from Feline Omentum Neutral Lipids

For this analysis, the neutral lipid fraction was obtained by applying 200 mg of a total omentum lipid extract (CMFr) dissolved in chloroform to a 10 gm silica gel column and eluting with 25 column volumes of chloroform. This fraction was analyzed for fatty acid content by gas chromatography-mass spectrometry (GC-MS). In order to liberate the fatty acids and form their methyl esters an aliquot (2.5 mg) of the neutral lipid fraction was dissolved in 0.67 ml of chloroform and 0.33 ml of 0.5 N methanolic sodium hydroxide was added. The sample was heated at 60° C. for one hour, cooled and mixed with 0.2 ml of water to form two phases. The upper phase was removed and discarded. The lower phase was evaporated to dryness with a stream of nitrogen. The fatty acid methyl esters (FAME) were redissolved in n-hexane for analysis by GC-MS.

A Finnigan 4500 GC-MS was used to analyse the FAME. Gas chromatography was performed on a 30 M ×0.25 mM methyl silicone bonded phase fused silica capillary column (DB-1, J & W Scientific, Inc.) with helium as the carrier gas at 12 psi. The column oven temperature was programmed from 205° C. to 300° C. at 2° C./min with the exit end placed directly into the ion source of the mass spectrometer. Mass spectrometry was performed in the electron impact mode (70 eV) with positive ion detection. Spectra were collected and stored at 0.5 sec intervals.

Injection of standard FAMEs demonstrated that under the conditions used, fatty acids with from 12 to 27 carbons could be detected. The sample yielded chromatographic peaks that were identified as 14:0–0.7%, 16:1–0.2%, 16:0–19.5%, 16:1–0.6%, 17.0–1.1%, 18:2–9.8%, 18:1–44.2%, 18:0–24.0% and traces of 15:0 and 17:2. The identities of the FAME peaks were established by comparison of their chromatographic elution properties and mass spectra to those obtained from standard compounds. The percentage composition for each peak (calculated from a chromatogram plotted from the total ion current of each spectra) is of the summed areas of all FAME peaks.

(2a) Preparation of the porcine and bovine CMFr

For preparation of porcine and bovine Chloroform Methanol Fraction (CMFr), fresh and/or frozen omentum was obtained from a local slaughterhouse. Omenta tissues were washed with minimum amount of distilled water, weighed and cut into 1–2 g pieces under sanitary conditions. Upon pooling and mixing of omenta pieces, they were divided into 500 g portions. Extra portions were kept frozen at −25° c. Each 500 g portion was homogenized with four times Phosphate Buffer Saline (PBS) in a glass blender at 22,000 RPM and for 2 min. the resultant homogenate was centrifuged (4000 RPM, 10 min., 5° c.), and the lipid cake was collected (about 98% of omentum weight). Solvent extraction (10 times chloroform: Methanol, 2:1) was carried out on the collected lipid cake in a glass blender (22,000 RPM, 30 s ). The organic solvent containing lipid was centrifuged (2,000 RPM, 20 min., 5° c.). Although most of the tissue residue was precipitated as pellet, some finer particles were still suspended after centrifugation. Consequently, attempts were made to collect the solvent phase with minimum tissue residues. The solvent extract was subjected to rotary evaporation (under vacuum, 37° C.) until dryness, i.e., neither any solvent condensation occurs, nor any solvent odor is present. The whitish CMFr weighing 70±2% of the omentum was then collected.

(2b) Preparation of the porcine and bovine HxCMFr

The chloroform/methanol fraction is warmed up to 37° C. Four times 95% EtOH (obtained from absolute ethanol) and six times hexane was added to the CMFr and mixed for 20 minutes. The mixture was then transferred to a separatory funnel, wherein the ethanol and hexane phases were allowed to separate in 20 minutes. Hexane and ethanol phases were separately collected. The ethanol phase was then back washed with 6 times hexane, shaken and allowed to separate. The hexane phase was back washed with 4 times 95% EtOH and the phases allowed to separate within 1 hour. If extra hexane is needed to facilitate the separation, it would be added. The collected ethanol and hexane phases seemed to consist of only one phase. However, upon storage of each phase at refrigerator temperature, (i.e., 4° c.), each of the collected phases was separated into two new ethanol and hexane phases which were again collected separately.

The total hexane phase is then subjected to rotary evaporation (under vacuum, 37° c.) until a translucent hexane extract of chloroform/methanol fraction is obtained (HxCMFr). The recovery of this phase is about 82±3% of CMFr. The extra product is stored at −25° c.

(2c) Analysis of fatty acids from porcine and bovine HxCMFr

Analysis of porcine and bovine HxCMFr was carried out with a method similar to that used for analysis of feline extract. Calculation of fatty acid composition of porcine and bovine HxCMFr from the preliminary chromatographic analysis showed the following composition:

| % Fatty Acid In Hexane Extract of Omentum | | |
|---|---|---|
| | Bovine | Porcine |
| Myristic Acid | 3.1 | 7.0 |
| Palmitolic Acid | 1.5 | 5.8 |
| Palmitic Acid | 27.1 | 27.1 |
| Linoleic Acid | 1.2 | 7.9 |
| Oleic Acid | 40.5 | 37.0 |
| Stearic Acid | 24.5 | 15.1 |

Other organic solvents can be used to extract omentum and the invention is not limited to the specific solvents mentioned above.

(2d) We also note the use of supercritical gas extraction for omentum fractions and factors as described in our co-pending application S.N. 793,622 filed Oct. 31, 1985 by Kamarei and hereby incorporated by reference. This application is now U.S. Pat. No. 4,749,522 issued June 7, 1988.

Here a supercritical fluid such as (SCF) $CO_2$ is used to extract omentum. An SCF has increased solvation power at temperatures above the critical pressure (Pc) and critical temperature (Tc).

$CO_2$ is used. Polar materials such as gangliosides remain in the residue while the extract contains the more non-polar or lipid materials such as triglycerides. Temperatures used for example are 38–39° C. and extractor pressures are about 3500 psig. Thus these conditions can avoid extraction using toxic materials, or inefficient extraction or use of expensive and time-consuming extractions and materials.

(2e) Use of Detergents for Lipid Isolation

Lipids are displaced from homogenized cell membranes, or other complexes involving proteins, by amphipathic detergent molecules which render the proteins "soluble" in aqueous media. The released lipid material is recovered by flotation after centrifugation.

A list of possible detergents is given in Tables I(a) and I(b). These are used in concentrations ranging from 0.1 to 2.0% (w/v) and a pH form 7.0 to 8.0.

(2f) Cryogenic methods for omental extraction can be used such as liquid $N_2$ for obtaining a finely divided omental material which can then be extracted with organic solvents such as above or directly with hexane, detergents or supercritical fluids such as $CO_2$ as described above. Other extraction or separation techniques can be used as well such as column chromatography, HPLC, affinity columns antibody columns, mild heat. Cryogenic separation is a subject of our copending application S.N. 811,507 filed Dec. 20, 1985. This application is now U.S. Pat. No. 4,776,173 issued Oct. 11, 1988.

(2g) Mild heat up to about 70° C. can also be used to extract omentum together with cryogrinding.

The examples herein are for illustrative purposes and are not meant to limit the invention which is contemplated to include extraction and use by whatever means of any mammalian omental materials; in therapy for skin conditions, in cosmetics, and in skin care use.

EXAMPLE I and II

Two subjects (a female age 42, and a male age 30) applied the feline omentum total lipid extract, which contains 99% triglycerides, once a day every other day for a period of one week.

TABLE 1 (a)

| | DETERGENTS WITH FLEXIBLE HYDROPHOBIC REGIONS | |
|---|---|---|
| Detergent type | Structural formula | Formal (and trivial) name |
| Strongly ionic | (structure: alkyl chain—$O-S(=O)_2-O^- Na^+$) | Sodium dodecylsulphate |
| | (structure: alkyl chain—$N^+(CH_3)_2-CH_2Br^-$) | Cetyltrimethylammonium bromide |
| "Weakly" ionic | (structure: alkyl—$N(CH_3)(CH_2COO^-Na^+)$, sarcosinate) | Sodium dodecyl-N—sarcosinate (sarkosyl) |
| Zwitterionic | (structure: alkyl—$N^+(CH_3)_2-CH_2-CH_2-CH_2-S(=O)_2-O^-$) | Sulfobetaine (Zwittergent)[a] Palmitoyllysolecithin |
| | (structure: alkyl—$C(=O)-O-CH_2-CH(OH)-CH_2-O-P(=O)(O^-)-O-CH_2-CH_2-N^+(CH_3)_3$) | |
| "Weakly" Zwitterionic | (structure: alkyl—$N(CH_3)_2 \rightarrow O$) | Dimethylalkylamine oxides (Ammonyx LO)[b] |

TABLE 1 (a)-continued
DETERGENTS WITH FLEXIBLE HYDROPHOBIC REGIONS

| Detergent type | Structural formula | Formal (and trivial) name |
|---|---|---|
| Non-ionic | ~~~~~O—[CH$_2$—CH$_2$—O]$_n$H | Polyoxyethylene alcohol (Brij series, Lubrol W.AL.P series) |
| | ~~~~—⌬—O—[CH$_2$—CH$_2$—O]$_n$H | Polyoxyethylene nonylphenol (Triton N series Igepal CO series Surfonic N series Emulgen series) |
| Non-ionic with branched hydrophobic region | ⎯⋀⎯⌬—O—[CH$_2$—CH$_2$—O]$_n$H | Polyoxyethylene p.t.octyl phenol (Triton X series Igepal CA series Nondet P40) |

[a]Available from Calbiochem-Behringer, Serva.
[b]Available from Onyx Chemical Co., 190 Warren Street, Jersey City NJ 07032 U.S.A.

TABLE 1 (b)
DETERGENTS WITH RIGID HYDROPHOBIC REGIONS

| Detergent type | Structural formula | Formal (and trivial) name |
|---|---|---|
| Strongly ionic | (steroid structure with OH, HO, OH, COO$^-$Na$^+$) | Sodium cholate |
| "Weakly" ionic | (steroid structure with C(=O)—NH—CH$_2$—CH$_2$—S(=O)$_2$—O$^-$Na$^+$) | Sodium taurocholate |
| Zwitterionic | (steroid with C(=O)—N—CH$_2$CH$_2$CH$_2$—N$^+$—CH$_2$CH$_2$CH$_2$—S(=O)$_2$—O$^-$) | CHAPS[a] |
| Non-ionic | (steroid with [2 Galactose, 2 Glucose, 1 Xylose] substituent) | Digitonin |

[a]3-[(3-cholamidopropyl) dimethylammonio]-1-propanesulphonate, available from Calbiochem-Behring, Serva.

The following observations were made at the end of the test period:

(a) the skin of the subjects appeared to be smooth to the touch and soft, (b) Small wrinkles and creases became visually reduced, (c) The skin remained moist for at least two weeks without the use of any hand creams and, (d) In addition, in one of the subjects' chronic calluses on the palm of the hand disappeared. The material was non-irritating to both subjects.

The observed effects may be attributed to the following biological effects: (a) repair of the damaged membrane of epithelial cells (lipid bilayer membrane) by the omental lipids so that the cells became more functional; (b) increase in microcirculation bringing a richer blood supply to the skin area. Enhancement of regional capillary blood supply may be perceived as contributing to the removal of noxious agents (e.g., products of bacterial growth) and in supplying essential nutrients to the cells and improved oxygen delivery; (c) activation of enzymes which are involved in the degradation of collagenous and keratinous deposits; and (d) neutralization of oxidizing agents (metabolic products and oxygenous sources) by providing an oxidizable substrate (E.G., fatty acid double bonds).

Therefore this total omental lipid fraction (CMFr) may be useful in a number of cosmetic applications such as skin creams, shampoos, soaps, sunscreens and deodorants. These creams can also be oils, ointments or liquid phase in nature. Also useful in eye creams, lip protectors. These protectors can be in oil or stick form. Use of the bovine material alone or in mixtures may enhance stick strength. Active outdoor sport protective cream, body moisturizer, day cream, night cream, after shave conditioner, and callus softener cream or lotion are also possible. We also have discovered that the CMFr serves to enhance healing of epithelial full thickness open skin wounds (these wounds included the underlying cutaneous muscles), for example in dogs. Therefore this material has a healing effect for example with respect to skin as seen in our co-pending application S.N. 805,206 filed Dec. 4, 1985 by Catsimpoolas and Sinn. This application is now U.S. Pat. No. 4,767,746, issued Aug. 30, 1988.

Topical application of the CMFr for example bovne or feline CMFr or HxCMFr did not irritate the wounds. This is considered an unexpected result since many substances which are like a cream, a lotion or an ointment irritate skin wounds. In fact early experiments showed that CMFr in Aquaphor ® base irritated the wounds. Healing of the wounds was shown upon application of the purified CMFr or HxCMFr alone and not in a base. Therefore use of omental fractions in cosmetics or skin care products may also exhibit a healing effect for minor cuts, sores, abrasions, or cracks often found in skin.

In addition, we have found the omentum CMFr useful in treatment of myocardial infarction as in our co-pending application S.N. 811,375 filed Dec. 20, 1985. This application is now U.S. Pat. No. 4,778,787 issued Oct. 18, 1988. CMFr material is also useful for bone healing as shown in our co-pending application S.N. 811,894, filed Dec. 20, 1985.

EXAMPLE III

The porcine hexane extracted lipid from omentum (PO HxCMFr) was used daily by two female subjects for several months. One subject reported the results included dramatically softer skin on face and hand together with imparting a consistent sheen to the skin. The cream produced excellent moisturizing benefits especially suited to benefit winter dry skin as an emollient. The cream can be used alone or together with a night cream.

The other subject reported after three months used of PO HxCMFr on hands, arms, legs and face that the material served as an excellent emollient especially smoothing and softening extra-dry summer tanned skin. The benefits are especially noted to be without concomitant use of sunblock in the face of sun, heat, salt and chlorine exposure. The material imparts a non-greasy glow to facial skin and saves dry, fair skin from flakiness caused by the above elements.

EXAMPLE IV

The Porcine hexane phase extract of the omentum (HxCMFr) was used on a male subject on the left arm daily for six weeks. Both arms were treated the same thereafter. The omental extract had the following effects on the skin of the left arm after six weeks: emollient, softening, reduction in white spots, smoothing and accelerated tanning. 7/7 witnesses observing the two arms noted the reduction in white spots and 6/7 of these witnesses noted the enhanced tanning in the left.

In addition the fingernails on the left arm were much smoother than those of the untreated right arm.

The porcine isolated materials were found to be better than the bovine since the porcine material from the hexane fraction dissolved easily on the skin. However, the bovine isolated lipid can cause desireable strengths for cosmetic products. Therefore the mixture of porcine and bovine products are useful as well.

EXAMPLE V

The Ames mutagenicity test (Ames et al. (1975) Mutation Research 31:347–364) performed on the porcine omentum extract (POCMFr) by Product Safety Laboratories of 725 Cranbury Rd, East Brunswick, New Jersey 08816. The mutagenic potential of the test material was measured by its ability to induce reverse ("Back") mutations in specially constricted strains of the bacterium *Salmonella Typhimuruim*. Mutagens which require activation by enzymes found in mammalian tissues are detected in the bacterial assay by the addition of mammalian microsomes (S-9 fractions).

Positive Controls

In the absence of metabolic activation, N-Methyl-N-nitro-N-nitrosoguanidine (MNNG), 9-aminoacridine (9AA), and 2-nitroflourene (2NF) were used with the appropriate strains. In the presence of metabolic activation, 2-amino-anthracene (2AA) was used as a positive control for all tester strains.

Negative Controls

The spontaneous mutability of each strain in the presence and absence of metabolic activation was determined. Solvent controls were used at the highest volume tested in the experiment.

The Salmonella/mammalian microsome assay of Ames (Ames et al., 1975) utilizes specially constructed strains of the bacterium, *Salmonella typhimurium*, to detect mutagenic activity of chemicals. The rationale for the test lies in the established correlation between mutaenic activity and carcinogenic potential, and, similarly, with birth defects and heritable disease.

Gene (point) mutations are usually recognized as change in a phenotypic characteristic. In the Ames assay, the dependence of the Salmonella tester strains on an exogenous source of histidine (auxotrophy) is altered by reverse mutation to histidine independence (prototrophy) In this particular system, the reversion occurs by either base-pair substitution or frameshift mutation, depending upon the strain. The various strains carry additional genetic markers which enhance their sensitivity to mutagens.

In the assay, tester strains are exposed to a series of doses of the test article at concentrations up to the highest practicable does within the limitations of toxicity or solubility. Mutagenic activity is manifested by an increase in the numbers of mutant colonies which grow in the absence of histidine, compared to the spontaneous (background) number of mutants. Mutagens which require activation by enzymes found in mammalian tissues, are detected in the bacterial assay by the addition of mammalian microsomes (S-9 fractions).

Ames Test Materials

Bacterial Indicator Strains

*Salmonella typhimurium* strains TA 1535, TA 1537, TA 1538, TA 98 and TA 100 were originally obtained from Dr. Bruce N. Ames, Berkeley, California. Strains were propagated in nutrient broth containing 0.5% NaCl, checked for appropriate genetic markers, and stored frozen (Revco freezer) after addition of DMSO (dimethyl sulfoxide) to approximately 8% final concentration.

Media

1. Mutrient broth (Difco) was supplemented with 0.5% NaCl.
2. Top agar contained 0.6% Difco agar, 0.5% Nacl, 0.5 mM biotin, and 0.5 mM L-histidine-HCl.
3. Minimal-glucose agar medium contained 1.5% Bacto-Difco agar in Vogel-Bonner Medium E (Vogel and Bonner, 1956) with 2% glucose.
4. Tryptone agar.

Positive Control Chemicals

N-methyl-N-nitro-N-nitrosoguanidine (MNNG), 9-aminoacridine (9-AA), and 2-nitrofluorene (2-NF) were used in the direct mutagenesis assay with indicator strains as shown in Appendix 1.

2-aminoanthracene (2-AA) was used with all strains in the assay with metabolic activation as shown in Appendix 2.

Solvent

Acetone was the solvent used for the test article.

1. S-9 Metabolic Activation Mixture

S-9 was thawed on the day of assay, diluted first in Tris-KCl buffer to a protein concentration of 10 mg/ml, then added to S-9 buffer to give a final concentration of 100 microliter S-9/ml. The complete S-9 mix was passed through a 0.45 um disposable Nalgene filter unit for sterilization and stored at approximately 4° C. until use on the same day.

The following components and their final concentrations were used in S-9 buffer:

| Component | Final Concentration/ml S-9 mix |
|---|---|
| MgCl$_2$ | 8 micromole |
| KCl | 33 micromole |
| Glucose-6-phosphate | 5 micromole |
| NADP | 4 micromole |
| NaH$_2$PO$_4$.H$_2$O, pH 7.4 | 100 micromole |

Methods for Ames Test

Bacterial Preparation

The cultures used in this assay were started from the frozen permanents in 21 ml of nutrient broth with 0.5% NaCl and incubated 12–16 hours on a shaker water bath at 37° C. The fresh cultures were stored in a refrigerator while tests for the appropriate genetic markers were conducted. These tests, which were carried out as described by Ames et al. (1975), showed no growth in the absence of histidine, and no growth in the presence of crystal violet or after exposure of ultraviolet light. Strains TA 1535, TA 1537 and TA 1538 were susceptible to ampicillin, while strains Ta 98 and TA 100 were resistant.

Preliminary Toxicity Testing

The effect of the test article on the survival of the bacterial strains was determined prior to the Ames bioassay. This was accomplished by adding 0.1 ml of different levels of the test article and solvent to tubes containing 2.0 ml top agar (at 45° C.) and 0.1 ml of the tester strain. After mixing, the tube contents were poured onto the surface of tryptone agar plates. The plates were incubated at 37° C. for 40–48 hours and the background lawn of bacteria in test article plates was compared to the bacterial lawn in the solvent plates. Toxicity on the tryptone agar plates was detectable by a thinning or disappearance of this background lawn of bacteria.

Plate Assay for the Detection of Direct Acting Mutagens

Assays were performed according to the method of Ames et. al. (1975). The test material was dissolved and diluted in solvent (acetone) on the day of the assay. The following were added, in order, to 2 ml of molten top agar (45° C.):

1. 0.1 ml of culture of the appropriate indicator strain;
2. 0.1 ml of the appropriate concentrations of test material, control article, or solvent.

Each tube was prepared individually, immediately vortexed, and the contents poured over the surface of a minimal-glucose agar plate. Each plate was rotated to evenly distribute the top agar before it hardened. All plates were incubated for approximately 48 hours at 37° C. After incubation, the plates were observed for revertant colonies and the colonies were counted and recorded.

Five doses of test article were tested in triplicate with each strain. Positive control articles for each strain and spontaneous revertant controls consisting of the indicator strains and solvent were run concurrently. The solvent and the highest dose level of the test material were checked for sterility by adding 0.1 ml of each to 2 ml of top agar without the test organisms and pouring the entire contents over minimal-glucose agar plates.

Plate Assay for the Detection of Mutagens Requiring Metabolic Activation

Plate assays with S-9 were conducted as described above, the only modification being the addition of 0.5 ml of S-9 mix to each tube of top agar immediately before vortexing and pouring.

The positive control article for each strain and spontaneous revertant controls consisting of the indicator strains and S-9 mix were run concurrently. The S-9 mix was checked for sterility by adding 0.5 ml to 2 ml of top agar without the test organisms and pouring the entire contents over minimal-glucose agar plates. All plates were incubated approximately 48 hours at 37° C.

Criteria

The following criteria were used in the evaluation and reporting of the mutagenic potential of the test material:

1. The spontaneous revertant levels for each strain when used in either the direct plate assay or the activated plate assay must not differ significantly from the range of historical values shown in Appendix 3.
2. All sterility controls must be negative.
3. All positive controls must demonstrate that the indicator strains are functional with known mutagens as evidenced by an increase of at least three times the number of revertant colonies per plate as the spontaneous revertant controls.
4. To be considered positive for mutagenic activity, the test material should exhibit a dose response effect (increasing number of revertant colonies with increased amounts of the test sample).
5. To be considered mutagenic for strains TA 1535, TA 1537, TA 1537, TA 1538, and TA 98, the test sample should produce a positive dose response over three concentrations with the lowest increase in revertants/plate greater than or equal to 3x the solvent control value or the S-9 fraction control value, as applicable.
6. To be considered mutagenic for strain TA 100, the test sample should produce a positive dose response over three concentrations with at least one dose producing an increase in revertants/plate greater than or equal to 3.5 x the solvent control value or the S-9 fraction control value, as applicable.

A valid test requires that criteria 1, 2 and 3 be met. To be considered mutagenic, criteria 4, and 5 or 6 must also be met.

AMES TEST
Appendix 1
POSITIVE CONTROL CHEMICALS IN THE DIRECT MUTAGENESIS ASSAY

| Indicator Strain | Positive Control Chemical | Conc. (ug/plate) | Solvent | Mutagenic Activity |
|---|---|---|---|---|
| TA 1535 | MNNG | 5.0 | DMSO | Base-pair Substitution |
| TA 1537 | 9-AA | 250.0 | DMSO | Frameshift Mutation |
| TA 1538 | 2-NF | 0.5 | DMSO | Frameshift Mutation |
| TA 98 | 2-NF | 0.5 | DMSO | Frameshift Mutation |
| TA 100 | MNNG | 5.0 | DMSO | Base-pair Substitution |

MNNG, N—methyl-N—nitro-N—nitrosoguanidine; 9-AA, 9-aminoacridine; 2-NF, 2-nitrofluorene; DMSO, dimethylsulfoxide.

AMES TEST
Appendix 2
POSITIVE CONTROL CHEMICALS IN THE METABOLIC ACTIVATION MUTAGENESIS ASSAY

| Indicator Strain | Positive Control Chemical | Conc. (ug/plate) | Solvent | Mutagenic Activity |
|---|---|---|---|---|
| TA 1535 | 2-AA | 2.5 | DMSO | Base-pair Substitution |
| TA 1537 | 2-AA | 2.5 | DMSO | Frameshift Mutation |
| TA 1538 | 2-AA | 2.5 | DMSO | Frameshift Mutation |
| TA 98 | 2-AA | 2.5 | DMSO | Frameshift Mutation |
| TA 100 | 2-AA | 2.5 | DMSO | Base-pair Substitution |

2-AA, 2-aminoanthracene; DMSO, dimethylsulfoxide.

AMES TEST
Appendix 3
HISTORICAL BACKGROUND OF SPONTANEOUS REVERTANT LEVELS FOR THE BACTERIAL INDICATOR STRAINS*

| Strain | Mean (# Revertants/ Plate) | Standard Deviation | Range (# Revertants/ Plate) |
|---|---|---|---|
| A. Plate Assay Without Metabolic Activation System | | | |
| TA 1535 | 18.09 | 8.04 | 2–43 |
| TA 1537 | 6.29 | 2.47 | 2–15 |
| TA 1538 | 13.72 | 4.48 | 5–32 |
| TA 98 | 23.54 | 9.03 | 9–60 |
| TA 100 | 144.94 | 41.89 | 66–318 |
| B. Plate Assay With Metabolic Activation System | | | |
| TA 1535 | 15.86 | 5.98 | 5–40 |
| TA 1537 | 8.19 | 2.68 | 2–15 |
| TA 1538 | 26.27 | 10.22 | 12–65 |
| TA 98 | 39.85 | 14.31 | 16–90 |
| TA 100 | 156.53 | 44.61 | 73–407 |

Mutagenic results

Porcine omentum (CMFr) was found to be nonmutagenic in both the direct and S-9 metabolic activation. Salmonella mutagenicity assay using Salmonella tester strains TA 1535, TA 1537, TA 1538, TA 98 and TA 100 when tested at concentrations of 10,000, 1,000, 100, 10 and 1 microgram/plate both without metabolic activation and with S-9 metabolic activation using acetone as the solvent. Cytotoxicity tests were caused out with strains TA 98 and TA 100 at concentrations of 10,000, 5,000, 1,000, 500 and 100 microgram/plate in an acetone solvent. No toxicity was observed at any of the levels tested. Plate incorporation tests were conducted in triplicate with and without S-9 liver microsome mix with the following concentrations of original sample per plate: 10,000, 5,000, 1,000, 500 and 100 microgram/plate.

EXAMPLE VI

Oral toxicity tests on the PO HxCMFr (white creme) were done by Product Safety Labs, 340 commercial Avenue, New Brunswick, NJ 08901. The test material was warmed under tap water until liquified.

During the test period the animals (rats) were each uniquely identified and individually housed in stainless steel wire bottomed cages in an environmentally controlled room with a 12 hour light/dark cycle. Feed and water were provided ad-libitum after dosing.

Procedure

Acute Oral Toxicity. FHSLA, 16 CFR 1500.3. The rats were fasted for 18 hours and then individually and singly dosed by gavage with 5.0 g/kg body weight of test material. The rats were individually caged and observed for mortality or other signs of gross toxicity for 14 days. Feed and water were provided ad-libitum.

The oral $LD_{50}$ of the Porcine HMFr test material is greater than 5.0 g/kg

EXAMPLE VII

Eye irritation studies were done on the PO HxCMFr and the BO HxCMFr (bovine omentum hexane extracted CMFr) on rabbits by Product Safety Labs of New Brunswick, NJ.

During the test period the six animals were individually housed in wire bottomed cages in an environmentally controlled room with a 12 hour light/dark cycle. Feed and water were provided ad-libitum after dosing.

Procedure

Primary Eye Irritation was done according to FHSLA 16 CFR 1500.42. Six healthy young adult albino rabbits were each uniquely identified. One-tenth of a milliliter (0.1 ml) of the test material was placed on the everted lower lid of one eye of each rabbit. The upper and lower lids were gently held together for 1 second before releasing, to prevent loss of the test material. The other eye of each rabbit remained untreated and served as a control. Ocular lesions were evaluated by the method of Draize et al. J. Pharmacol. Exp. Ther. 83:337–390, 1944. The Draize scores were then classified according to Kay and Callandra, J. Soc. Cos. Chem. 13:281–289, 1962. Lesions were evaluated at 24, 48 and 72 hours.

| MMTS* | Classification | Symbol |
|---|---|---|
| 0.0–0.5 | Non-irritating | N |
| 0.6–2.5 | Practically non-irritating | PN |
| 2.6–15.0 | Minimally irritating | $M_1$ |
| 15.1–25.0 | Mildly irritating | $M_2$ |
| 25.1–50.0 | Moderately irritating | $M_3$ |
| 50.1–80.0 | Severely irritating | S |
| 80.1–100.0 | Extremely irritating | E |
| 100.1–110.0 | Maximally irritating | $M_x$ |

*maximum mean total score

The MMTS of the PO HxCMFr was 1.00. The material is considered to be practically non-irritating (PN).

The MMTS of the BO HxCMFr was 0.00. The test material is considered to be non-irritating.

EXAMPLE VIII

The objective is to determine the potential of a material to induce skin sensitization. This test may be useful in eliciting potent sensitizers.

Prophetic Patch Test

Material is applied to the subject's back under the dressing and kept in place for 48 hours. The test site is graded at 15 minutes and 24 hours after the removal of the dressing. Two weeks after the first application a patch is left in place for 48 hours, removed and graded 15 minutes and 24 hours later according to the following scale:

| SCORING SCALE | |
|---|---|
| X | Not Patched |
| 0 | No reaction |
| 0.5 | Minimal reaction |
| 1 | Definite erythema |
| 2 | Erythema with edema |
| 3 | Erythema with vesiculation and edema |
| 4 | Intense Erythema with bullae |
| G | Glazing |
| S | Scaling |

Subjects 100 healthy human adults free of any significant systemic or dermatologic disorder. The area of the back utilized is free of any blemishes which might interfere with grading the test sites. Written informed consent is obtained from are subjects prior to the start of a test.

Prophetic patch test was done on 100 subjects by Derma-test Laboratories Inc., 29–28 41st Avenue, Long Island City, Ny 11101 on bovine chloroform-methanol extract CMFR and bovine omentum hexane extracted CMFr (BOHxCMFr). 0.15 ml of the extracts are used. Also tested was 0.15 ml petrolatum on 102 subjects using Parke-Davis patch material. In the induction phase, patches were removed and sites scored 48 and 72 hours after application; all test materials were negative at each reading. Challenge patches were applied 12 days after removal of the induction patch readings were made at 48 and 72 hrs. After application all patch sites were negative at each reading without any evidence of dermal contact irritation or sensitization.

Repeated insult patch test by Derma-Test was done on PO HxCMFr and PO CMFr on 102 subjects using Webril occluded by Scanpor with Blenderm as the patch material. Induction patches were removed and sites scored 48 hours after application (0.15 ml) for ten consecutive application. Challange patches were as above, same scale as above. Under the conditions of the test there was no evidence of either dermal contact irritation or sensitization.

EXAMPLE IX

Many formulations of lotions and creams are possible. We present several possible formulations for lotion which were successful in terms of stability, and appearance as a pure white material and give no separation at 50° C.:

| CTFA NAME | LOTION INGREDIENTS (2-17C) TRADE NAME | SUPPLIER* | AMOUNT (%) |
|---|---|---|---|
| Omentum (Porcine HxCMFr) | | Angio-Medical | 20.00 |
| Sorbitan Stearate | Span 60 | ICI | 4.06 |
| Propylparaben | Propylparaben | Mallinckrodt | 0.10 |
| Polysorbate 60 | Tween 60 | ICI | 2.94 |
| Glyceryl Stearate | Myverol 18-07 | Eastman Kodak | 1.50 |
| Tocopheryl Acetate | Vitamin E Acetate | Hoffman La Roche | 0.20 |
| Dimethicone | Dow Corning 200, 300 cps | Dow Corning | 5.00 |
| Carbomer 940 | Carbopol 940 | B. F. Goodrich | 0.07 |
| Water | Purified Water USP | | 40.16 |
| Butylene Glycol | 1,3 Butylene Glycol | Union Carbide | 5.00 |
| Methylparaben | Methylparaben | Mallinckrodt | 0.30 |
| Trisodium EDTA | Trisoium EDTA | Dow | 0.10 |
| Phenoxyethanol | Emeressence 1160 | Emery | 0.50 |
| Triethanolamine | Trietanolamine | Union Carbide | 0.07 |
| Sodium Hyaluronate | Actigan HY (1%) | Active Organics | 20.00 |
| | | | 100.00 |

*Mallinkrodt-Chemical Co., P.O. Box 5439 St. Louis, Mo 63147 ICI/Concord Pike/New Murphy Rd. Wilmington DC 19817 Eastman Kodak/343 State ST,/Rochester NY 14650 Hoffman LaRoche/340 Kingsland St/Nutley, N.J. 07110 Dow Corning/P.O. Box 1767/Midland, MI 48640 B F Goodrich/6100 Oaktree Blvd/Cleveland, Ohio 44131 Union Carbide/Old Ridgebury Rd/Danbury, CT 06817 Dow Chemical Co/2020 Dow Centre/Midland Mi 48640 Emery/1300 Carew Tower/-Cinncinati Ohio 45202 Active Organics/7715 Dinsmore Ave /Van Nys Calif 91406

| | Omentum Lotion (2-23D) |
|---|---|
| Deionized Water | 50.85 |
| Butylene Glycol | 5.00 |
| Methylparaben | 0.30 |
| Trisodium EDTA | 0.10 |
| 2% Carbopol 940 Solution | 3.50 |
| Omentum | 15.00 |
| Span 60 | 3.05 |
| Propylparaben | 0.10 |
| Tween 60 | 2.20 |
| Myverol 18-07 | 1.13 |
| Vitamin E | 0.20 |
| Dow Corning 200 Fluid | 1.00 |
| Triethanolamine 99% | 0.07 |
| Phenoxyethanol | 0.50 |
| 1% Sodium Hyaluronate Solution | 15.00 |
| Dow Corning 200 Fluid | 2.00 |
| | 100.00 |

We also disclose three possible cream formulations as follows also stable at 50° C.:

| | Cream 2-19A | | Cream 2-19B | |
|---|---|---|---|---|
| | % | g/200 g | % | g/200 g |
| Omentum | 35 | 70 | 35 | 70 |
| Span-60 | 5 | 10 | 5 | 10 |
| Propylparaben | 0.1 | 0.2 | 0.1 | 0.2 |
| Tween 60 | 3.5 | 7.0 | 3.5 | 7 |
| Myverol 18-07 | 1.5 | 3.0 | 3.0 | 6 |
| Vitamin E (Tocopheryl Acetate) | 0.2 | 0.4 | 0.2 | 0.4 |
| Distilled Water | 38.65 | 77.3 | 37.15 | 74.3 |

-continued

| | Cream 2-19A | | Cream 2-19B | |
|---|---|---|---|---|
| | % | g/200 g | % | g/200 g |
| 2% Carbopol 940 solution | 7.5 | 15.0 | 7.5 | 15 |
| 1,3-Butylene Glycol | 5.0 | 10.0 | 5.0 | 10 |
| Methylparaben | 0.3 | 0.6 | 0.3 | 0.6 |
| Trisodium EDTA | 0.1 | 0.2 | 0.1 | 0.2 |
| Phenoxy ethanol | 0.5 | 1.0 | 0.5 | 1.0 |
| TEA 99% | 0.15 | 0.3 | 0.15 | 0.3 |
| Dow Corning 200 | 2.5 | 5.0 | 2.5 | 5.0 |
| | pH | 6.19 | pH | 6.25 |

| | Omentum Cream 2-19C |
|---|---|
| Deionized Water | 19.33 |
| Butylene Glycol | 5.00 |
| Methylparaben | 0.30 |
| TriSodium EDTA | 0.10 |
| 2% Carbopol 940 Solution | 12.50 |
| Omentum | 25.00 |
| Span 60 | 3.57 |
| Propylparaben | 0.10 |
| Tween 60 | 2.50 |
| Myverol 18-07 | 2.15 |
| Vitamin E | 0.20 |
| Dow Corning 200 Fluid | 1.00 |
| Triethanolamine 99% | 0.25 |
| Phenoxyethanol | 0.50 |
| 1% Sodium Hyaluronate Solution | 25.00 |
| Dow Corning 200 Fluid | 2.50 |
| | 100.00 |

TABLE II

COMPARISON OF 20% OMENTUM CREAMS (5% Silicone, no hyaluronate)

| Rakuma Batch # | Reza Sample # (Extraction Method) | Date Made | pH | Viscosity (#4 Spindle 3 RPM - cps) | 45° C. Emulsion Stability | Emulsion Thickening Temp. | Odor | Skin Feel |
|---|---|---|---|---|---|---|---|---|
| #98-61 | #6 (cryo-grind, thermal extract) | 12/3 | 6.80 | 54,000 | Still OK 12/13/85 | 41° C. | Sl. Fatty | Somewhat heavy, almost oily initially. Goes quickly to a velvety/waxy end-feel. |
| #98-62 | #3 (cryo-grind, Super Crit. CO$_2$ extract) | 12/3 | 6.75 | 47,000 | Still OK 12/13/85 | 44° C. (thins at 37° C.) | Neutral | Light initial feel fatty). Cream feels "moist" as apply, then goes directly to velvety rich end feel. |

TABLE II-continued

COMPARISON OF 20% OMENTUM CREAMS
(5% Silicone, no hyaluronate)

| Rakuma Batch # | Reza Sample # (Extraction Method) | Date Made | pH | Viscosity (#4 Spindle 3 RPM - cps) | 45° C. Emulsion Stability | Emulsion Thickening Temp. | Odor | Skin Feel |
|---|---|---|---|---|---|---|---|---|
| #98-63 | #2 (cryo-grind, hexane extract) | 12/3 | 6.80 | 45,000 | Still OK 12/13/85 | 44° C. (thins at 36° C.) | V. Sl Fatty | Initial waxiness, somewhat heavy. Then goes quickly to velvety (sl. oily) final rich feel. High sheen on skin. |
| #98-64 | #1 (chloroform/ Methanol, then Ethanol) | 12/3 | 7.20 | 45,000 | Still OK 12/13/85 | 42° C. | Distinct (pleasant) | Softer texture than #98-63; spreads easier on skin (leaves thinner film). Very quick "absorption". Sl. d nice end feel. |
| #98-65 | #4 (hexane) | 12/3 | 6.90 | 37,000 | Still OK 12/13/85 | 38° C. (slight) | Neutral | Lubrous initial feel (sl. dry). End feel is lovely - rich, barely waxy, not heavy. |

NOTES:
(1) All creams above have high gloss and long "peak".
(2) Omentum Sample #4 was fluid; all others were solid.
(3) Omentum Sample #1 to be eliminated from consideration for cost reasons.
(4) Of all the creams above, RLG prefers #98-62 (Omentum Sample #3) for overall skin feel.

It will be obvious to those skilled in the art to vary proportions in said lotions or creams. It is also possible to use various lipid omental extracts or fractions. From the experience with the lotion one should add hyaluronate to the cream as hygroscopic agent or other agents besides silicone or tutylene glycol. The presence of omental lipid plus hyaluronate has an increased or synergistic effect on skin, enhancing still further the smoothness of the skin after treatment with said combination of materials.

It will also be obvious to use other silicone agents such as diphenyl silicone or methyl-phenyl silicone or cyclomethicone for dimethicone. It will also be obvious to use other emulsifiers other than glycerol stearate, sorbitan stearate, carbomer or polysorbate 60 or other preservatives than methylparaben, propylparaben, EDTA or phenoxyethanol or other antioxidants than EDTA or Vitamin E. The omentum can be included in the lotion up to about 30% whereas the cream can probably contain up to about 80% omentum material. There is also whipped omentum which is 100% omentum which can also include some silicone. Therefore, it is contemplated the invention encompasses all cosmetic or skin care formulations containing omental material.

Other methods as described above used to extract omentum, as for example, porcine, can be used to produce creams or lotions. Table II shows these different creams wherein:

Reza Sample (#1 400 grams of porcine neutral lipids (HxCMFr, batch #35 and 36-85-P.O.) from omentum powder. This source is obtained by initial extraction which chloroform/methanol followed by removal of polar lipids, via ethanol extraction, from the extract.

Reza Sample (#2) 300 grams of porcine neutral lipids (HxFr, batch #37-85-P.O.) from omentum powder. This source is obtained directly by hexane extraction of omentum powder.

Reza Sample (#3) 300 grams of SuperCritical-$CO_2$ extract of porcine omentum powder (equal portions of V8 and V9 extracts of the last 3 runs).

Reza Sample (#4) 300 grams of Angio-Medical porcine subcutaneous adipose tissue i.e. P.S.A.T. (batch #38-85). This source is directly extracted by hexane (HxFr).

Reza Sample (#5) 50 grams of Angio-Medical P.S.A.T. (batch #15-85-F.B.). This source which should be similar to sample #4, is extracted by SuperCritical $CO_2$ (V8).

Reza Sample #6 500 grams of thermally extracted porcine omentum powder (batch #39-85-P.O.).

Each cream in Table II was made identically using the same propellor and phase addition temperatures (75° C. water phase added to 75° C. oil phase) as in 17-C. above using water instead of hyaluronate. All creams were jarred at 35° C. and viscosity measured after one week.

EXAMPLE X

It appears the omental material has a bacteriocidal effect. Tests were done by Liberco Testing Inc., 123 Hawthorne St., Roselle Park, New Jersey 07204 on feline CMFr as below:

Method of Assay

U.S.P. XXI Antimicrobial Preservative Effectiveness Page 1151.

| Microbial Challenge Test | ATCC # |
|---|---|
| Staphylococcus Aureus | 6538 |
| Pseudomonas Aeruginosa | 9027 |
| Escherichia Coli | 8739 |
| Candida Albicans | 10231 |
| Aspergillus Niger | 16404 |

The bacteria employed in this study were maintained as broth cultures and the molds were grown on agar slants. 0.1 ml. of a 24 hour broth culture of the test bacteria and 0.1 ml. of 100 ml. of a washing of an agar slant were added to 20 ml. of the sample and well mixed. The samples were stored at room temperature for the entire test period. After storage for 2 days, 1 week, 2 weeks, 3 weeks and 4 weeks a portion of the incubated sample was removed and plated by the serial dilution method. The bacteria were plated on tryptic soy agar with letheen and incubated for 48 hours at 35° C. Yeast and molds were plated on potatoe dextrose agar with letheen and incubated at room temperature for 1 week. The plates were examined for survivors and the percent reduction, against the original number of organisms added, was calculated.

At the same time the test was set up, 0.1 ml. of the test organisms were added to 20 ml. of sterile peptone water. This was immediately plated out to determine the number of organisms added to the sample. This is the culture control.

| 2% CARBOPOL 940 SOLUTION | |
|---|---|
| Deionized Water | 97.70 |
| Methylparaben | 0.20 |
| Propylparaben | 0.10 |
| Carbopol 940 | 2.00 |
| | 100.00 |

| RESULTS: | S. AUREUS | P. AERUGINOSA | E. COLI | C. ALBICANS | A. NIGER |
|---|---|---|---|---|---|
| 0 HOUR COUNT/ML. | 270,000 | 320,000 | 220,000 | 300,000 | 140,000 |
| 2 DAYS COUNT/ML. | <10 | >30,000 | <10 | >30,000 | 120 |
| % REDUCTION | 99.99+ | <90.62 | 99.99+ | <90.00 | 99.91 |
| 1 WEEK COUNT/ML. | 35 | >300,000 | <10 | <10 | 35 |
| % REDUCTION | 99.99 | 0 | 99.99+ | 99.99+ | 99.97 |
| 2 WEEKS COUNT/ML. | <10 | 23,000 | <10 | <10 | <10 |
| % REDUCTION | 99.99+ | 92.81 | 99.99+ | 99.99+ | 99.99+ |
| 3 WEEKS COUNT/ML. | <10 | <10 | <10 | <10 | <10 |
| % REDUCTION | 99.99+ | 99.99+ | 99.99+ | 99.99+ | 99.99+ |
| 4 WEEKS COUNT/ML. | <10 | <10 | <10 | <10 | <10 |
| % REDUCTION | 99.99+ | 99.99+ | 99.99+ | 99.99+ | 99.99+ |

EXAMPLE XI

There is a manufacturing procedure for the omental lotion or creme which endows the lotion or creme with a superior slip decreasing the stickiness or drag of the lotion or cream wherein some of the silicone material component is added at the end so as not to be part of the emulsion as follows:

Manufacturing Procedure for Omentum Lotion and Cream

Step 1

In a suitable size beaker, add the required amount of Deionized Water and Butylene Glycol and start heating to 70–75° C. Add Methylparaben, and Trisodium EDTA and mix until dissolved. Add the 2% Carbopol 940 solution. Continue mixing and maintain temperature at 70–75° C.

Step 2

In a separate beaker, add the ingredients of the oil phase: Omentum, Span 60 (Sorbitan Monostearate), Propylparaben, Tween 60 (Polysorbate 60), Myverol 18–07 (Glyceryl Stearate), Vitamin E (Tocopheryl Acetate) and Dow Corning 200 fluid. Bring the temperature to 75° C. while mixing to uniformity. DO NOT OVERHEAT.

Step 3

Add the oil phase into the main beaker while mixing. Add Triethanolamine then Phenoxyethanol into the batch. Continue mixing the batch. Begin cooling the batch down to 30° C.

Step 4

Add Actigen HY (1% Sodium Hyaluronate) into the batch at 45° C. Mix gently.

Step 5

Continue cooling and gently mixing the batch. Add Dow Corning 200 fluid into the batch at 33° C. Stop cooling the batch at 30° C.

Procedure for 2% Carbopol 940 Solution

In a suitable size stainless steel pot, heat Deionized Water to 70–80° C. Turn on turbomixer or high shear mixer and sprinkle Methylparaben and Propylparaben. Check that the Methylparaben and Propylparaben are completely dissolved. Add Carbopol 940 using a small scoop at a time. Mix to uniformity until Carbopol 940 is completely dissolved. Stop turbomixer and cool the batch to 30° C. using propeller mixer.

EXAMPLE XII

Hyaluronate can be added as a mixture of components of different molecular weights to combine the maximum amount of slip (by inclusion of hyaluronate of high molecular weight of about 1,000,000) while maximum absorption of hyaluronate into the skin is achieved by including hyaluronate(s) of low molecular weight of less than 100,000 or about 1,000–10,000.

EXAMPLE XIII

The omental material is found to have a soothing, healing action on skin conditions. Topical treatment with omental material, for example the PO HxCMFr or POCMFr, (also known as Activa ® lotion or creme) healed irritation skin rash and excema conditions.

Also it is used for keratosis condition to remove or smooth bumps. Seborrhea is also a possible target condition to be treated.

EXAMPLE XIV

In order to investigate the presence of any possible viruses in the porcine omentum CMFr, comprehensive viral profile was performed by Damon Clinical Lab. on two such samples (batch #25-B-85 and 25-C-85-P.O.; Bioprocessing assay #51 and 52). Porcine omentum CMFr was prepared according to the protocol described under 2a (Page 10).

| Comprehensive viral studies Includes isolation, identification and serotyping (when applicable) of the following viruses: | |
|---|---|
| Adenovirus Group | Influenza A, B and C |
| Cytomegalovirus | Lymphocytic Choriomeningitis (LCM) |
| Enteroviruses | Mumps |
| Coxsackie A | Parainfluenza (serotypes 1–4) |

-continued

| Comprehensive viral studies |
| Includes isolation, identification and serotyping (when applicable) of the following viruses: |

| (23 serotypes) | |
| Coxsackie B (serotypes 1-6) | Rhinovirus |
| Echovirus (serotypes 1-30) | Rubella (German measles) |
| Poliovirus (serotypes 1-3) | Rubeola (measles) |
| Herpes simplex virus (types 1 and II) | Varicella zoster |

The results were reported as: "no virus isolated".

What is claimed:

1. A topical cosmetic composition for skin care consisting essentially of an omental lipid and a cosmetic agent in a stable cosmetic formulation selected from the group consisting of a cream, shampoo, oil, lotion, sunscreen, deodorant, powder, moisturizer, soap, solid, stick and ointment.

2. The composition of claim 1 wherein the cosmetic agent comprises at least two materials selected from the group consisting of sorbitan stearate, propylparaben, polysorbate 60, glyceryl stearate, tocopheryl acetate, dimethicone, carbomer 940, water, butylene glycol, methylparaben, trisodium EDTA, phenoxyethanol, triethanolamine, and sodium hyaluronate.

3. Composition of claim 1 further comprising gangliosides.

4. The composition of claim 1 wherein the cosmetic agent is selected from at least one of the group of silicones, hyaluronates, emulsifiers, preservatives, hygroscopic agents, anti-oxidants, metal chelating agents, skin fillers and skin barriers.

5. The composition of claim 4 wherein the chelating agent is ethylenediamine tetracetic acid.

6. The composition of claim 4 wherein the skin filler is Carbomer.

7. The composition of claim 4 further comprising hyaluronate mixtures of molecular weights in the range 1,00–1,000,000 daltons.

8. The composition of claim 4 wherein the emulsifiers are selected from the group of glycerol stearate, sorbitan stearate, carbomer, polysorbate 60 and mixtures thereof.

9. The composition of claim 4 wherein the anti-oxidant is selected from the group of EDTA, Vitamin E, BHA, BHT, BHQ and mixtures thereof.

10. The composition of claim 4 wherein the preservative is selected from the group of methylparaben, propylparaben, phenoxyethanol, butylene glycol, EDTA and mixtures.

11. The composition of claim 4 wherein the hygroscopic agent is selected from the group of silicone compounds, butylene glycol, hyaluronate compounds, water and mixtures thereof.

12. The composition of claim 11 wherein the silicone compound is selected from the group consisting of dimethicone, diphenicone, phenyldimethicone, cyclomethicone and mixtures thereof.

13. The composition of claim 4 wherein the skin barrier is a silicone compound.

14. The composition of claim 13 wherein the silicone skin barrier compound is selected from the group consisting of dimethicone, diphenicone, phenylmethicone, cyclomethicon and mixtures thereof.

15. Composition of claim 1, wherein the omental lipids are mammalian omental lipids selected from the group of carnivora, cetacea, sirenia, primate, chiroptera, proboscidea, edentata, rodentia, insectivora, perissodactyla, artrodactylas and mixtures thereof.

16. Composition of claim 15 wherein the mammalian omental lipids are selected from the group of equine, porcine, feline, ovine, bovine and mixtures thereof.

17. The composition of claim 16 further comprising silicone.

18. The composition of claim 16 further comprising hyaluronate.

19. A topical cosmetic composition for skin care consisting essentially of an omental lipid and a cosmetic agent in a stable cosmetic formulation selected from the group consisting of a cream, shampoo, oil, lotion, sunscreen, deodorant, powder, moisturizer, soap, solid, stick and ointment and wherein the cosmetic agent is selected from at least one of the group consisting of a silicone, a hyaluronate, an emulsifier, a preservative, a hygroscopic agent, an anti-oxidant, a metal chelating agent, a skin filler and a skin barrier.

20. A topical cosmetic composition for skin care consisting of 20% omentum material and a cosmetic agent composition consisting of

| Cosmetic Agent | Amount (%) |
| --- | --- |
| Sorbitan Stearate | 4.06 |
| Propylparaben | 0.10 |
| Polysorbate 60 | 2.94 |
| Glyceryl Stearate | 1.50 |
| Tocophenryl Acetate | 0.20 |
| Dimethicone | 5.00 |
| Carbomer 940 | 0.07 |
| Water | 40.16 |
| Butylene Glycol | 5.00 |
| Methylparaben | 0.30 |
| Trisodium EDTA | 0.10 |
| Phenoxyethanol | 0.50 |
| Triethanolamine | 0.07 |
| Sodium Hyaluronate | 20.00 |
| | 100.00 |

21. A topical cosmetic composition for skin care consisting of 15% omentum material and a cosmetic agent composition consisting of

| Cosmetic Agent | Amount (%) |
| --- | --- |
| Deionized Water | 50.85 |
| Butylene Glycol | 5.00 |
| Methylparaben | 0.30 |
| Trisodium EDTA | 0.10 |
| 2% Carbopol 940 Solution | 3.50 |
| Span 60 | 3.05 |
| Propylparaben | 0.10 |
| Tween 60 | 2.20 |
| Myverol 18-07 | 1.13 |
| Vitamin E | 0.20 |
| Dow Corning 200 Fluid | 1.00 |
| Triethanolamine 99% | 0.07 |
| Phenoxyethanol | 0.50 |
| 1% Sodium Hyaluronate Solution | 15.00 |
| Dow Corning Fluid | 2.00 |
| | 100.00 |

22. A topical cosmetic composition for skin care consisting of 35% omentum and a cosmetic agent composition consisting of

| Cosmetic agent | % | g/200 g |
|---|---|---|
| Span-60 | 5 | 10 |
| Propylparaben | 0.1 | 0.2 |
| Tween 60 | 3.5 | 7.0 |
| Myverol 18-07 | 1.5 | 3.0 |
| Vitamin E (Tocopheryl Acetate) | 0.2 | 0.4 |
| Distilled Water | 38.65 | 74.3 |
| 2% Carbopol 940 solution | 7.5 | 15.0 |
| 1,3-Butylene Glycol | 5.0 | 10.0 |
| Methylparaben | 0.3 | 0.6 |
| Trisodium EDTA | 0.1 | 0.2 |
| Phenoxy ethanol | 0.5 | 1.0 |
| TEA 99% | 0.15 | 0.3 |
| Dow Corning 200 | 2.5 | 5.0 |

23. A topical cosmetic composition for skin care consisting of 35% omentum and a cosmetic agent composition consisting of

| Cosmetic agent | % | g/200 g |
|---|---|---|
| Span-60 | 5 | 10 |
| Propylparaben | 0.1 | 0.2 |
| Tween 60 | 3.5 | 7.0 |
| Myverol 18-07 | 3.0 | 6.0 |
| Vitamin E (Tocopheryl Acetate) | 0.2 | 0.4 |
| Distilled Water | 37.15 | 77.3 |
| 2% Carbopol 940 solution | 7.5 | 15.0 |
| 1,3-Butylene Glycol | 5.0 | 10.0 |
| Methylparaben | 0.3 | 0.6 |
| Trisodium EDTA | 0.1 | 0.2 |
| Phenoxy ethanol | 0.5 | 1.0 |
| TEA 99% | 0.15 | 0.3 |
| Dow Corning 200 | 2.5 | 5.0 |

24. A topical composition for skin care consisting of 25% omentum and a cosmetic agent composition consisting of

| Cosmetic agent | Amount % |
|---|---|
| Deionized Water | 19.33 |
| Butylene Glycol | 5.00 |
| Methylparaben | 0.30 |
| TriSodium EDTA | 0.10 |
| 2% Carbopol 940 Solution | 12.50 |
| Span 60 | 3.57 |
| Propylparaben | 0.10 |
| Tween 60 | 2.50 |
| Myverol 18-07 | 2.15 |
| Vitamin E | 0.20 |
| Dow Corning 200 Fluid | 1.00 |
| Triethanolamine 99% | 0.25 |
| Phenoxyethanol | 0.50 |
| 1% Sodium Hyaluronate Solution | 25.00 |
| Dow Corning 200 Fluid | 2.50 |
| | 100.00 |

* * * * *